(12) United States Patent
Cabrerizo et al.

(10) Patent No.: US 10,188,869 B2
(45) Date of Patent: Jan. 29, 2019

(54) HARDWARE/SOFTWARE INTEGRATED DESIGN FOR A 3D TREMOR DETECTOR USING TMS IN PARKINSON'S DISEASE AND RELATED DISORDERS

(71) Applicants: Mercedes Cabrerizo, Miami, FL (US); Malek Adjouadi, Miami, FL (US); Niovi Rojas, Miami, FL (US); Juan Omar Perez, Miami, FL (US); Anastasio A. Cabrera, Bradenton, FL (US); Jesus De La Rua, Miami, FL (US)

(72) Inventors: Mercedes Cabrerizo, Miami, FL (US); Malek Adjouadi, Miami, FL (US); Niovi Rojas, Miami, FL (US); Juan Omar Perez, Miami, FL (US); Anastasio A. Cabrera, Bradenton, FL (US); Jesus De La Rua, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 636 days.

(21) Appl. No.: 14/803,839

(22) Filed: Jul. 20, 2015

(65) Prior Publication Data

US 2016/0015994 A1  Jan. 21, 2016

Related U.S. Application Data

(60) Provisional application No. 62/026,792, filed on Jul. 21, 2014.

(51) Int. Cl.
*A61N 2/00* (2006.01)
*A61B 5/00* (2006.01)
(Continued)

(52) U.S. Cl.
CPC ............ *A61N 2/006* (2013.01); *A61B 5/1101* (2013.01); *A61B 5/486* (2013.01); *A61B 5/4836* (2013.01);
(Continued)

(58) Field of Classification Search
None
See application file for complete search history.

(56) References Cited

U.S. PATENT DOCUMENTS

| 7,974,696 B1 * | 7/2011 | DiLorenzo | A61B 5/0476 607/2 |
|---|---|---|---|
| 2003/0074032 A1 * | 4/2003 | Gliner | A61B 5/0484 607/45 |

(Continued)

OTHER PUBLICATIONS

Heumann, Rolf et al., "Dyskinesia in Parkinson's disease: mechanisms and current non-pharmacological interventions." *Journal of Neurochemistry*, Aug. 2014, 130(4): 472-489.

(Continued)

*Primary Examiner* — Thaddeus Cox
*Assistant Examiner* — Joshua D Lannu
(74) *Attorney, Agent, or Firm* — Saliwanchik, Lloyd & Eisenschenk

(57) ABSTRACT

Systems that integrate Transcranial Stimulation Biofeedback (TSB) Detector functions and Transcranial Magnetic Stimulation (TMS) functions, as well as methods of manufacturing such systems and methods of performing TSB detection and TMS using such systems, are provided. A system can include a hardware component and a software component in operable communication with the hardware component. The hardware component can include or be in operable communication with a TMS machine, and the software component can be configured to receive waveforms from the TSB Detector hardware.

19 Claims, 3 Drawing Sheets

(51) Int. Cl.
*A61B 5/11* (2006.01)
*A61N 2/02* (2006.01)
(52) U.S. Cl.
CPC ........... *A61B 5/4082* (2013.01); *A61B 5/7225* (2013.01); *A61N 2/02* (2013.01)

(56) References Cited

U.S. PATENT DOCUMENTS

2013/0338483 A1* 12/2013 Neuvonen .......... A61B 5/04012
600/411
2014/0257427 A1*  9/2014 Marnfeldt .......... A61N 1/36067
607/45
2016/0008632 A1*  1/2016 Wetmore ................. A61N 7/00
601/2

OTHER PUBLICATIONS

Topka, H. et al., "A cerebellar-like terminal and postural tremor induced in normal man by transcranial magnetic stimulation." *Brain*, Aug. 1999, 122(8): 1551-1562.

* cited by examiner

HARDWARE/SOFTWARE INTEGRATED DESIGN FOR A 3D TREMOR DETECTOR USING TMS IN PARKINSON'S DISEASE AND RELATED DISORDERS

CROSS REFERENCE TO RELATED APPLICATION(S)

This application claims the benefit of U.S. Provisional Application Ser. No. 62/026,792, filed Jul. 21, 2014, which is hereby incorporated by reference in its entirety, including any figures, tables, or drawings.

GOVERNMENT SUPPORT

The subject invention was made with government support under a research project supported by the National Science Foundation Award No. CNS-0959985. The government has certain rights in this invention.

BACKGROUND OF INVENTION

Human tremors are some of the most common movement disorders. Human tremors can be associated with several factors, such as ageing and certain neurological disorders, including Parkinson's Disease (PD). PD is a degenerative disorder of the central nervous system resulting from the death of dopamine-generating cells in the substantia nigra leading to movement-related and, later, cognition-related symptoms.

Transcranial Magnetic Stimulation (TMS) is a safe and non-invasive method that affects the cerebral cortex but not deep structures. TMS uses electromagnetic induction by means of a rapidly changing magnetic field to induce weak electric currents that provoke activity in specific or diffuse parts of the brain. TMS causes depolarization or hyperpolarization in the neurons of the brain and can be used to investigate causality in the brain-behavior relationship.

Single/paired-pulse TMS depolarizes and discharges the action potential in the region that is being stimulated. When applied to the motor cortex, single/paired-pulse TMS can provoke motor evoked potentials. A variant of TMS is repetitive TMS (rTMS), which produces more durable effects after the initial stimulation. rTMS can increase or decrease the excitability of the corticospinal tract depending on the intensity of stimulation, coil orientation, and frequency.

An excitatory effect of TMS in one area may (through inhibitory interconnections) induce inhibition of a different area. TMS techniques can be used to diagnose movement disorders and as a therapeutic tool in PD. For example, studies have indicated increased inhibition in patients with PD following TMS suggesting that cortical excitability is reduced.

Previous studies in PD patients have shown that rTMS can reduce impairment in PD. For example, at rTMS frequencies of 5 Hz and higher, enhanced motor cortex excitability was observed, whereas lower frequencies of 1 Hz and lower transiently depressed cortical excitability.

BRIEF SUMMARY

The subject invention provides hardware-software assimilated systems to evaluate the efficacy of the repetitive Transcranial Magnetic Stimulation (rTMS) on patients with Parkinson's Disease (PD) and related disorders before, during, and/or after the stimulation-based treatment.

Embodiments of the subject invention provide integrated Tremor Sensor TMS systems that can control magnetic stimulation of the brain according to selected moments in the tremor cycle, as well as methods of manufacturing such systems and methods for performing tremor detection and TMS using such systems. If the magnetic stimulus from a TMS is not adequately adjusted to the patient-specific tremor frequency, there is the potential that the expected outcome may not be completely achieved, but the same stimulus can reduce or suppress the tremor if the magnetic stimulation is adequately adjusted. Systems of the subject invention can ensure the latter result.

Systems of the present invention can be integrated and non-invasive, and can include two essential and fully adapted components: (1) a hardware design solution to detect, acquire and store data collected in three dimensions (X, Y, and Z); and (2) a software module that serves dual purposes: (i) to acquire the tremor signals, process the information, and synchronize the trigger of the TMS via the hardware components, and (ii) to serve as a graphical user interface (GUI).

The goal to be achieved with this integrated three-dimensional Tremor-Stimulation-Biofeedback (TSB) Detector device is to control the magnetic stimulation of the brain according to the given tremor frequency of a patient.

DETAILED DISCLOSURE

Figure 1:
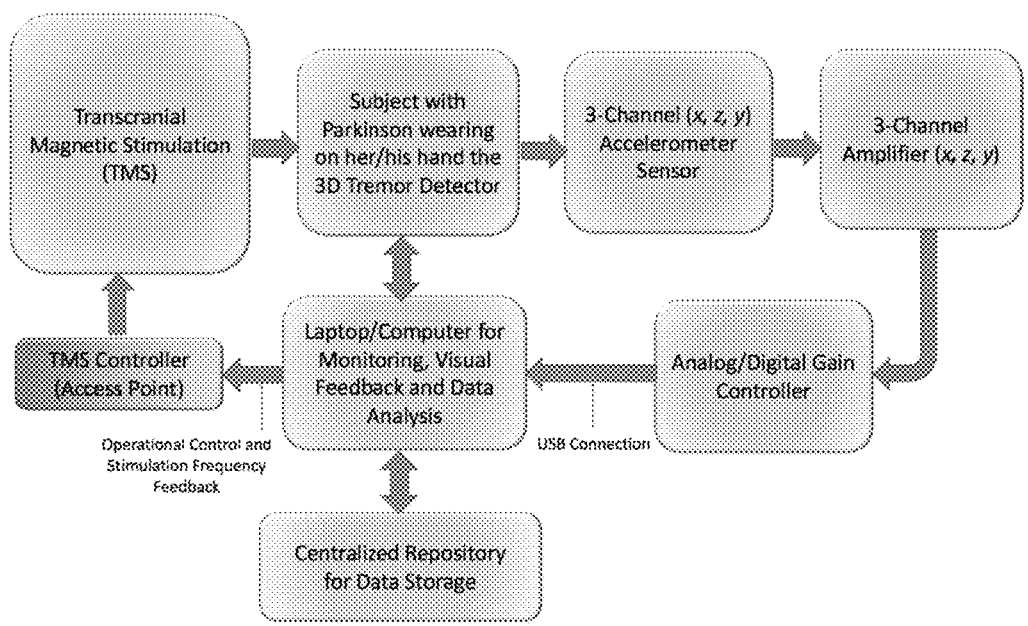
FIG. 1 illustrates a block diagram of a three-dimensional tremor detector design integration.

The subject invention provides hardware-software assimilated systems to evaluate the efficacy of the repetitive Transcranial Magnetic Stimulation (rTMS) on patients with Parkinson's Disease (PD) and related disorders before, during, and/or after the stimulation-based treatment.

In one embodiment, the subject invention provides a multimodal signal processing device with hardware-software integration comprising a three-dimensional Tremor-Stimulation-Biofeedback (TSB) Detector comprising a three-axes accelerometer sensor and a Transcranial Magnetic Stimulation (TMS) machine that allows to control the magnetic stimulation of the brain according to the given tremor frequency of a patient. The integrated TSB Detector-TMS system enables appropriate diagnosis and provides a means for early intervention and treatment of neurological diseases including movement disorders such as PD.

Advantageously, the subject invention provides a low-cost device to detect, quantify, and classify human tremors and evaluate the efficacy of rTMS in patients with PD and related disorders before, during, and after stimulation-based treatment.

Embodiments of the subject invention include a hardware-software integrated design that aligns in time and space a tremor accelerometer sensor with a neuro-navigated TMS machine. Time and space alignment refer to the opportunity for simultaneous recordings of tremor frequency and length under repeated TMS while using the same three-dimensional coordinate system on a same patient.

This integrated and non-invasive system of the subject invention can include the following fully-adapted components: (1) a hardware design solution that detects, acquires, and stores data collected in three dimensions (X, Y, and Z), and can automatically activate solenoids of TMS pedals for different operational functions (e.g. for four different operational functions); and (2) a software module.

In one embodiment, the hardware design can activate solenoids of TMS pedals for the following operational functions: (1) increase intensity of the magnetic pulse; (2) decrease intensity of the magnetic pulse: (3) trigger the electromagnetic pulse with a predefined intensity of the pulse; and (4) abort stimulation (e.g. if any undue effects are seen on the TSB Detector).

In one embodiment, the software module can serve the following purposes: (i) acquire the tremor accelerometer sensor signal, process the information and synchronize the trigger of the TMS via the hardware component, a synchronization which can be made in relation to a specific patient-based frequency of the recorded tremor in order to adjust the TMS output to the patient-specific tremor; and (ii) serve as a graphical user interface (GUI) for user-machine interaction. The GUI can guide the development of patient-specific mechanisms required for biofeedback treatment with cognitive protocols that are developed through empirical evaluations during training sessions.

In a preferred embodiment of the subject invention, the tremor accelerometer sensor is conveniently placed in the patient's hand. In further embodiments the tremor accelerometer sensor can be comfortably attached, for example, to the patient's foot, arm or leg.

In a preferred embodiment, the tremor frequency for each patient is detected and calculated and, based on such tremor frequency, the repetition rate of the magnetic stimulation is determined as a function of the recorded tremor while continuously monitoring the tremor signal; the intensity of the pulse is determined for each individual as a percentage of the resting motor threshold (RMT). The behavior of the deflections of the tremor signal in response to the magnetic brain stimulation can aid in predicting and assessing the reliability of the stimulation protocol.

In a further preferred embodiment, the goal of the customized display of the tremor frequency on the GUI is to enable a patient to control and, over time eventually eliminate, his/her tremor. In a further preferred embodiment, the subject invention includes a real-time biofeedback mechanism amenable for self-control training sessions.

Embodiments of the subject invention provide hardware-software assimilated systems that align, in time and space, tremor accelerometer sensor signals with the neuro-navigated TMS (e.g. TMS machine), as well as methods of manufacturing such systems, methods for integrating tremor accelerometer sensor signals and TMS functionalities, and methods of performing tremor accelerometer signal measurements and TMS using such systems. A system of the subject invention can be integrated and non-invasive and can include a hardware component that can automatically activate pedals of the TMS machine to, for example, perform different operational functions, including increasing intensity, decreasing intensity, and triggering a magnetic pulse.

It should be noted that although solenoids can be used to control the existing pedals from a commercially available TMS machines, in one embodiment of the invention, control signals can be provided to the TMS machine controller that will cause a TMS pulse to be generated, a TMS pulse to be increased in intensity, or a TMS pulse to be decreased in intensity by the TMS machine without the need for pedals to be used in a manual fashion. The control signals can also be controlled based on tremor signal in order to provide the patient a much safer experience when being subjected to TMS therapy.

In certain embodiments, the system can also include a software component, stored on one or more computer-readable media (e.g. non-transitory media), that can serve at least the purposes of: reading the tremor accelerometer signal and synchronizing the trigger of the TMS machine via the hardware component, a synchronization which can be made in relation to any of the deflections of the recorded tremor accelerometer signal (e.g. in order to suppress the tremor during stimulation); and serving as a GUI for a user of the system. The GUI can guide the development of patient-specific mechanisms required for biofeedback treatment with cognitive protocols that are developed through empirical evaluations during training sessions.

In one embodiment, the subject invention integrates the three dimensional tremor signals of a patient into the TMS machine via a dual communication link between the patient-specific frequency of the tremor in on direction (patient to machine), and brain stimulation in the other direction (machine to patient). This bidirectional link provides synchrony between the frequency observed in the tremor signal and the TMS parameters to be selected to ensure the most appropriate sessions for training and biofeedback.

In a preferred embodiment, the subject invention provides a state of the art tremor detector software module capable of acquiring and analyzing data in real time and automatically issuing the appropriate control signals for the selection of the parameters for the most appropriate TMS mode of operation (intensity of the stimulation and frequency of the magnetic pulse).

Systems of the subject invention can provide new understanding on how information flow is best synchronized between a tremor detector and TMS in both directions, as well as affirm the necessary precautions needed to be considered by physicians and technical staff when performing brain magnetic stimulation (e.g. single pulse or repetitive) in a wide range of applications.

FIG. 1 is a block diagram of a TSB-TMS system according to an embodiment of the subject invention. Referring to FIG. 1, the TSB-TMS includes a hardware component and a software component, which can be stored on one or more computer-readable media (e.g. non-transitory media). One or more connections can be provided to connect the hardware component and the software component. The hardware component and the software component can be configured to send signals to each other and receive signals from each other.

Figure 3:
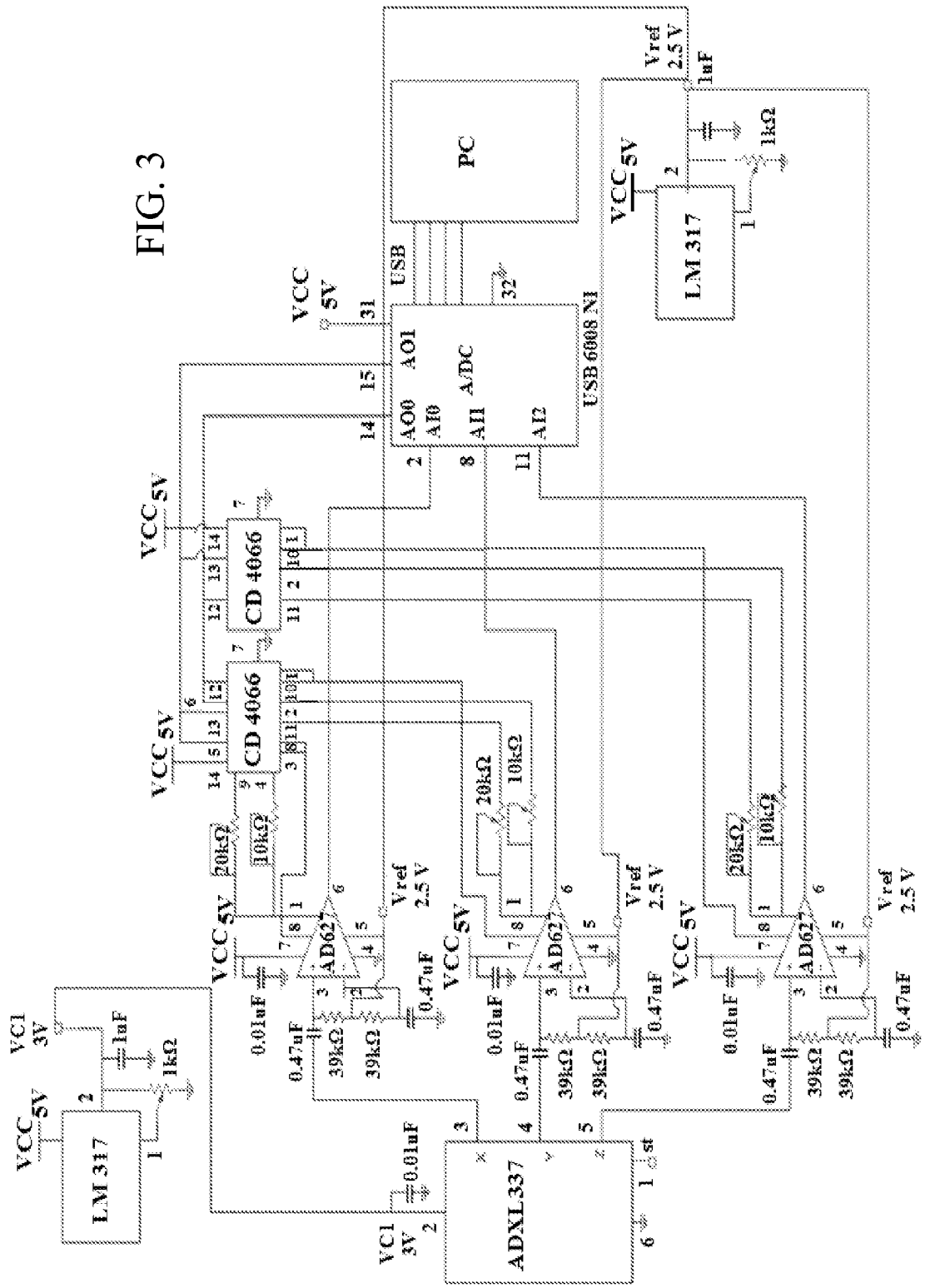
FIG. 3 illustrates electronic elements of an integrated tremor detector design.

FIG. 3 shows a schematic of a hardware circuit according to an embodiment of the subject invention. Referring to FIG. 3, the hardware component includes a hardware circuit, such as an integrated circuit, having one or more circuit elements (e.g. resistors, diodes, transistors, capacitors, relays, NAND gates, timers, solenoids). In certain embodiments, a hardware circuit can be operably connected to a TMS machine and/or TSB Detector hardware. The hardware circuit can receive signals from the software component and relay them to the TMS machine and/or the TSB Detector hardware to perform the desired functions and can receive signals from the TMS machine and/or TSB Detector hardware and relay them to the software component.

In a further embodiment, the TSB Detector hardware and/or TMS machine can be considered part of the hardware component. The TSB Detector hardware can include typical TSB Detector components known in the art.

In preferred embodiments, a compact and light-weight three-axes accelerometer sensor (ADXL 337) is conveniently placed in the patient's hand or attached to the patient's arm or leg to detect frequency of the arm and/or leg movements, and generate a low level voltage signal in the three coordinate axes (X, Y, and Z). The three-dimensional signals generated by the patient's tremor-related movements in the accelerometer are amplified in a three-channel analog amplifier (AD627), wherein the gain of the amplifier is controlled by the computer software through an analog switch (CD 4066). In further embodiments, two voltage regulators can feed the necessary voltage to the accelerometer and the three-channel amplifier.

In a preferred embodiment, the three-dimensional signal can be coupled to the computer through a 12-bit analog to digital converter and visualized in real time on a computer screen and/or stored for processing.

In a preferred embodiment, capacitors combined with resistors can provide a low cut-off frequency of 12 Hz to cope with the established tremor frequencies (2-12 Hz). For example, tremor associated with PD has a frequency in the range of 4-12 Hz. Based on the input from the tremor accelerometer sensor the software component can determine the frequency and consequently the intensity of the stimulation to be administered via the TMS machine.

In further preferred embodiments, a software component automates the control of the amplifier and the analog to digital converter to monitor the patient's hand and/or leg tremor in real time. The amplitude versus time of the three channels (according to the three coordinates X, Y, and Z) can be displayed on the computer monitor for visual interpretation and to follow the evolution of the patient's tremor during the training and biofeedback phases. In certain embodiments, the signals during these phases are recorded and stored for processing, analysis, and follow up to gauge the evolution of the patient's recordings over time. In a preferred embodiment, the 3D signals of the patient's hand tremor that are recorded in real time can be displayed, based on the accelerometer's output, on the computer screen for a more realistic biofeedback process.

In one embodiment, the 3D TSB Detector-TMS device of the subject invention detects and calculates the tremor frequency for each patient and customizes the number of repetitions of the magnetic stimulation as a function of the recorded frequency. In a preferred embodiment, several rTMS pulses can be induced through the cortex using, for example, an eight-shape magnetic coil.

In a further embodiment, the neuro-navigated TMS machine can use spatially co-registered anatomical Magnetic Resonance Imaging (MRI) to enable the visualization and functional mapping of the brain with a high accuracy.

In one embodiment, the calculation and full integration of the tremor intensity and frequency with the TMS system allows the precise tremor analysis of patients with PD and related neurological disorders and the non-invasive patient-specific brain stimulation through magnetic waves. In a preferred embodiment, this multimodal system allows for the appropriate intensity and repetition rate of the stimulation while continuously monitoring the tremor signals in three different directions under patient-specific training and biofeedback conditions. In this patient-specific way a more efficient training session can be administered to the patient with the aim of controlling the tremors and in time eventually eliminating the tremors completely. In a preferred embodiment, the subject invention also includes a real-time biofeedback mechanism amenable for self-control training sessions In a further embodiment, the deflections of the tremor signal in response to the magnetic brain stimulation can predict and assess the reliability of the protocol to be followed.

In one embodiment, the hardware circuit includes a TMS machine and may optionally include the TSB Detector hardware. In preferred embodiments, the software component communicates (i.e. sends signals to and receives signals from) directly with the TMS hardware and/or the TSB Detector hardware.

In certain embodiments, the TMS machine includes pedals. The pedals can be used to increase the intensity of the TMS machine, decrease the intensity of the TMS machine, and trigger a magnetic pulse of the TMS machine. The TMS machine can include, for example, three or more pedals, though embodiments are not limited thereto. For example, the TMS machine can include three pedals, and each pedal can perform one function out of: increasing the intensity; decreasing the intensity; and triggering a magnetic pulse.

In a further embodiment, the TMS machine or the hardware circuit of the TSB Detector-TSM includes one or more solenoids. The solenoids can be used to control the pedals, and one solenoid can be present for each pedal. For example, the TMS machine can include three pedals, and a first solenoid can trigger a first pedal which increases the intensity, a second solenoid can trigger a second pedal which decreases the intensity, and a third solenoid can trigger a third pedal which triggers a magnetic pulse.

In a preferred embodiment, the tremor accelerator sensor-generated signal can lead to an output trigger signal to the TMS controller. In one embodiment, the TMS controller is a hardware-software integrated design that given a digital signal can output a mechanical force automatically to the input pedals of the TMS machine.

In preferred embodiments, the subject invention allows collection of data simultaneously across different recording modalities and enables functional brain mapping of the motor cortex in direct relation to a tremor, including a PD-related tremor.

In many embodiments, the subject invention provides a complete product that fully integrates brain stimulation to a tremor detector device performing in real time the following operations: (1) synchronization of the tremor signals with the TMS; (2) acquisition and analysis of the tremor signals; (3) artifact removal; and (4) conversion of the saved signals to ASCII format for compatibility with other interfaces.

In preferred embodiments of the subject invention, an external module operates the TMS and selects automatically the stimulation frequency based on the harmonics of the patient's tremor. In a further preferred embodiment, the external control occurs from a portable computer.

In certain embodiments of the subject invention, the software component can include a software module stored on one or more computer-readable media (e.g., non-transitory media). The software component can be stored on, for example, a compact disc (CD), digital video disc (DVD), flash memory device, volatile memory, or a hard disk drive (HDD), such as an external HDD or the HDD of a computing device.

In many embodiments, the software component is used via a computing device, and the software is either stored on a portion of the computing device (e.g., HDD or volatile memory) or is on a computer-readable medium being read by the computing device. A computing device can be, for example, a laptop computer, desktop computer, server, a cell phone, or tablet, though embodiments are not limited thereto. A user can operate the software component through a GUI of the software component, which allows the user to interact with the software via the computing device. In one embodiment, the software is a closed-source C Sharp (C#) programming software module. The GUI of the software component can be configured to allow a user to set which frequency of brain stimulation is best suited for which tremor frequency.

In one embodiment, the software component is stored on a laptop computer, tablet, or desktop computer. In a particular embodiment, the software component is stored on a laptop computer.

In many embodiments, the software component is specifically designed and configured to interact with the hardware component and to allow a user to operate the hardware component through the GUI of the software component. A user can operate a TMS machine of the hardware component to, for example, increase the intensity, decrease the intensity, trigger a magnetic pulse, cease (abort) the stimulation function, turn the TMS machine on, or turn the TMS machine off. Similarly, a user can operate the TSB Detector hardware to perform any type of tremor recording using all frequencies of tremor or a subset of them, for example, ceasing function, turning on, and turning off the tremor recording system. These functions can be accomplished, for example, by the user entering a command through the GUI which the software component then relays to the hardware component. Such a command can be input by, for example, using a computing device which has the software component stored thereon or is reading the computer-readable medium having the software component to input the command. The software component then transmits a signal to the hardware component (e.g., to the hardware circuit, the TMS machine, and/or the TSB Detector hardware) to perform the input function.

In one embodiment, the software component is configured to relay a command for increasing the intensity, decreasing the intensity, or triggering a magnetic pulse of a TMS machine by sending a signal to depress pedals of the TMS machine. The pedals can be depressed, thereby causing the TMS machine to perform the desired function. Such signals can be sent to solenoids to trigger the pedals. In an alternative embodiment, the software component is configured to send signals directly to the processing center of the TMS machine (either through the hardware circuit or not) to cause it to increase the intensity, decrease the intensity, trigger a magnetic pulse, cease function, turn the TMS machine on, or turn the TMS machine off.

In many embodiments, the software component is configured to relay a command to TSB Detector hardware by sending a signal to the TSB Detector hardware. Such signals can be sent directly to the processing center of the TSB Detector hardware (either through the hardware circuit or not). Also, the software component can be configured to receive signals from the TSB Detector hardware and save the signals to the computer-readable medium on which the software component is stored or to a computer-readable medium with which the software component is in operable communication. The signals can be saved in any suitable format, for example, ASCII format.

In many embodiments, the software module of the software component is configured to acquire and analyze TSB Detector data in real time and automatically issue the appropriate control signals for the selection of the TMS mode of operation.

The software component and the hardware component can be connected to each other through connection between the hardware component and a computing device, the computing device either having the software portion stored thereon or being in operable communication with a computer-readable medium on which the software portion is stored. The hardware component and the computing device can be connected to each other using any suitable means known in the art. For example, the hardware component and the computing device can be connected to each other using wires (e.g., universal serial bus (USB) wires, serial wires, fire wire, etc.) or through wireless communication (e.g., through a wireless network and/or using a wireless transmitter and wireless receiver), though embodiments are not limited thereto. If using wires, such wires can connect to the hardware component and/or the computing device using ports provided thereon, including but not limited to, USB ports, serials ports, and fire wire ports. In one embodiment, such a computing device can be considered to be part of the software component.

In many embodiments, the software component is configured to automatically abort any TMS stimulation, any TSB Detector procedure, or both, if a determination factor falls outside a predetermined normal range. The software component is configured to receive signals from the hardware component and computes (e.g., periodically or continuously) multiple values to monitor any TMS stimulation and/or TSB Detector procedure. One or more determination factors can be set ahead of time by a user, as can acceptable (or normal) ranges for each determination factor. If a determination factor falls outside the normal range, the software component automatically sends a signal to the TMS stimulation machine (either through the hardware circuit or not), the TSB Detector hardware (either through the hardware circuit or not), or both, to abort. Such an abort can include shutting off and/or ceasing function. In a further embodiment, such an abort can include simply decreasing intensity.

In many embodiments of the subject invention, a TMS stimulation can be aborted when an unforeseen event is recorded (e.g. a determination factor is outside a normal range), and such an unforeseen event can be tied to any perturbation in the recorded tremor. A perturbation can be a change over the baseline that is deemed significant, for example, such a change can be in a value of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, or more. The change in percent over the baseline can be set differently for healthy controls and subjects with ailments and under clinical supervision with a reduced tolerance (smaller percentage) for subjects with ailments and under clinical supervision. According to embodiments of the subject invention, acceptable values or ranges for determination factors can be set or changed by a user at any time, before or during operation. Thus, one or more determination factors and acceptable values and ranges for those determination factors can be set on a patient-by-patient basis.

In one embodiment, a method of manufacturing a TBS Detector-TMS device includes providing a software component as described herein to a computing device and connecting the computing device to a hardware component as described herein. Providing the software component to the computing device can include installing the software component on the computing device (e.g., on an HDD of the computing device) or providing a computer-readable medium having the software component stored thereon to the computing device such that the computing device is in operable communication with the computer-readable medium.

In one embodiment, a method of performing TBS detection and TMS stimulation on a patient includes providing a TBS Detector-TMS as described herein in operable communication with a TMS machine and TBS Detector hardware connected to the patient, performing TMS stimulation on the patient, and monitoring TBS Detector-recorded tremor waveforms of the patient provided by the TBS Detector hardware. The waveforms can be monitored by the software component of the TBS Detector-TMS and/or by a user interfacing with a GUI of the software component. The user can interface with the GUI using a computing device having the software component stored thereon or in operable communication with a computer-readable medium having the software component stored thereon. If a determination factor based on the TBS detected tremor waveforms, falls outside an acceptable range, the software component automatically aborts the TMS stimulation. The user can adjust the determination factor(s) and the acceptable range for each determination factor at any time. Also, the user can manually increase the intensity, decrease the intensity, or trigger a magnetic pulse of the TMS machine using the GUI.

Embodiments of the subject invention advantageously provide easy and automated control of a TMS machine using a GUI. TBS Detector output can be monitored to adjust the TMS machine accordingly. An automatic abort function can be provided within the software module to abort TMS stimulation if a determination factor moves outside an acceptable range, thereby providing enhanced safety for the patient.

Embodiments of the subject invention also allow for safe and easy evaluation of the effects of brain stimulation on the electrical activity of the brain. A TMS machine can be used for stimulation while waveforms from TBS Detector hardware can be monitored for evaluation purposes and for safety purposes. An automatic abort function of the software module, as described herein, can provide further safety. The precise synchronization of the two modalities (brain stimulation and tremor signal analysis) according to embodiments of the subject invention augments the capabilities and interpretation of TMS-induced changes to the tremor.

Additionally, embodiments of the present invention fully integrate brain stimulation with TBS detection. A TBS Detector-TMS according to the subject invention is capable of performing in real time the following operations: (1) synchronization of the TBS Detector with the TMS machine; (2) acquisition and analysis of the TBS detected tremor; (3) artifact removal; (4) conversion of the saved TBS detected tremor signal to ASCII format for compatibility with other interfaces.

Further, embodiments of the present invention can have broad advantages for hospitals and research centers. New hypotheses can be tested and new interpretations of the TMS induced changes in the tremor of a patient with neurological condition can be considered, with the potential for new research findings and scientific insights. This unique approach, of the subject invention, at collecting data simultaneously across different recording modalities can help lead to a new understanding of the functional brain mappings of the motor cortex in direct relation to tremors, and can help refine theoretical and design premises. Also, the increased knowledge of the human brain that will result from the subject technology can help promote scientific discovery while ensuring at all times the well-being of the patient.

Moreover, embodiments of the subject invention can also be used with spatially co-registered anatomical Magnetic Resonance Imaging (MRI), so that engineers, scientists, and clinicians can visualize and delineate functional mappings of the brain with high accuracy. Moreover, due to the integration of TBS detection with a TMS machine, precise analysis and interpretation of the TBS detected tremor signal provide a more complete assessment of a given patient ensuring harmony between non-invasive brain stimulation through magnetic waves and the TBS detected tremor signal. Such a multimodal system allows for the appropriate timing for safe delivery of the brain stimulation, while continuously monitoring the TBS detected tremor signal. The same mechanism which automates the different functions of the TMS can also abort the stimulation if any unwarranted effects are observed in the TBS detected tremor signal. Many patients can benefit from the subject technology, including those with PD, other neurological disorders and metabolic disorders.

In addition, embodiments of the subject invention advantageously allow for synchrony between any of the deflections observed in the TBS detected tremor signal and the timing at which point brain stimulation can be given in the safest way possible, while continuously monitoring the TBS detected tremor signal for any unforeseen effect, with the added ability of aborting the stimulation process if the latter case arises.

Further, embodiments of the subject invention allow for real time monitoring and diagnosis, based on the TBS detected tremor signal deflections. With this added real-time analysis, a wider spectrum of different scenarios can be observed on the TBS Detector, in context to the administered brain stimulation, and can help promote the study of and may lead to diagnoses of related conditions.

In some embodiments, the TBS Detector-TMS system including the graphical user interface that allows a user to control the TBS Detector-TMS can be incorporated into a TMS machine so that the functionality provided by the TBS Detector-TMS can be integrated and potential cost savings in manufacture can be attained.

In some embodiments, TBS detected or other patient-related information can be inputted into the TMS with integrated TBS Detector-TMS capability in order to control the TMS pulses as discussed above.

Although TMS stimulation has been discussed herein, other magnetic stimulation to a patient that might affect the patient's tremor can also be controlled with embodiments of the invention.

The methods and processes described herein can be embodied as code and/or data. The software code and data described herein can be stored on one or more computer readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); or other media now known or later developed that is capable of storing computer-readable information/data. Computer-readable media should not be construed or interpreted to include any propagating signals.

EXAMPLES

Following are examples that illustrate embodiments and procedures for practicing the invention. These examples should not be construed as limiting.

Example 1

A TBS Detector-TMS was manufactured. FIG. 1 shows the hardware and software components of the TBS Detector-TMS. The TBS Detector-TMS was designed to interface with a TMS machine having three pedals as commercially available, one for increasing intensity, one for decreasing intensity, one for triggering a magnetic pulse. The TBS Detector-TMS was also designed to interface with TBS detector hardware such that TBS detected tremor signals are provided to the software component.

Figure 2:
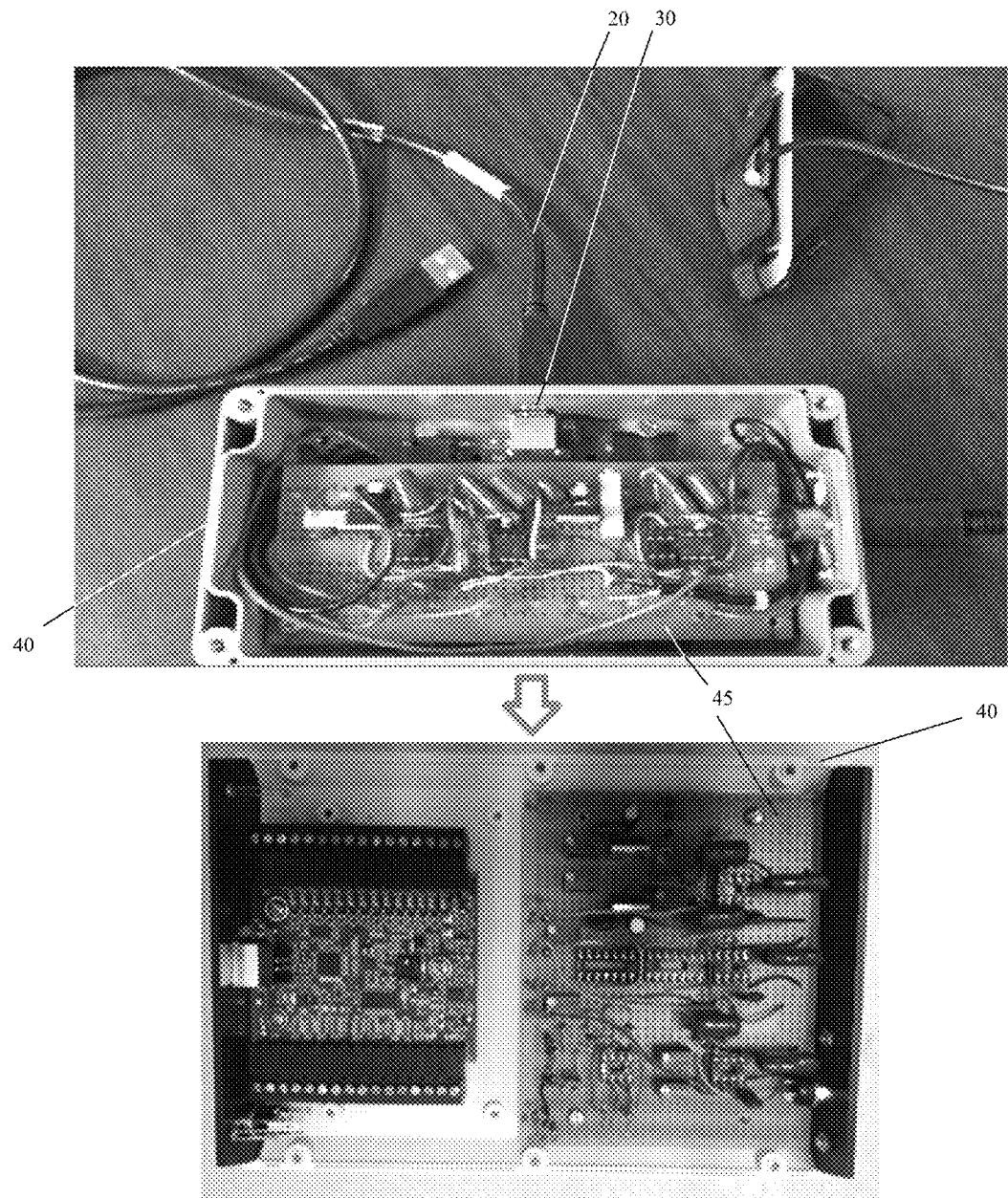
FIG. 2 illustrates the main components of an integrated three-dimensional tremor detector design.

Referring to FIG. 2, the TBS Detector-TMS has a software component installed on the HDD of a laptop computer and is connected via a USB cable 20 to a port 30 of the hardware component 40, which includes a hardware circuit 45. A circuit diagram of the hardware circuit 45 is shown in FIG. 3. The circuit 45 includes the following components:
A three-Axes Accelerometer Sensor (ADXL 337): This compact and lightweight sensor is especially designed to be attached to the arms or legs of any given patient to detect the intensity and frequency of the arm movements, and generates a low level voltage in the 3 coordinate axes (X, Y, and Z).
A three-Channel Amplifier (AD 627): The 3-dimensional (X, Y, and Z) signals generated by the movement of the patient in the accelerometer will be conveniently amplified in the 3-channel analog amplifier. The gain of the amplifier will be controlled by the computer software.
LM 317 (1): This voltage regulator will feed the necessary voltage (3v) to the accelerometer (ADXL337).
LM 317 (2): This voltage regulator will feed the reference voltage (−2.5v) to the 3-Channel amplifier (AD 627).
Analog to digital converter (A/DC): The 3-dimensional (X, Y, Z) signal is coupled to the computer through a 12-bit analog to digital converter. The signals can be visualized in real time and stored for processing.
Capacitors (0.47 µf) and resistors (39 KΩ): These capacitors combined with the resistors will provide the low cut off frequency of 12 Hz to cope with the established tremor frequencies (2-12 Hz).
CD 4066: This analog switch will control the gain to each of the amplified channels.

Example 2

Experiments were conducted using the TBS detector-TMS described in Example 1. Subjects were tested following a protocol defined as follows. The Nexstim's rTMS was employed in full integration with the TSB tremor detector system, where the r in front of the TMS denotes the option for the more elaborate repetitive pulse stimulation process. The TBS Detector device was placed through a comfortable and flexible band in the patient's hand. Three recording signals in the three-dimensional coordinate system were obtained. A 10-minute baseline before and after stimulation were recorded. Blood pressure was monitored throughout the entire experiment.

Five-minute repetitive stimulation (SR=6 Hz (or multiple of the calculated hand tremor), intensity is 50% of the highest intensity reached by the coil) sequence was followed allowing for five stimulations and five one-minute intervals of no stimulation. The motor cortex was stimulated using three electrode sites F3, FC3 and C3 for the left hemisphere positioning the coil in the horizontal position perpendicular to the cortex sulcus being stimulated.

Tremor signals were displayed on a monitor and the patient was asked to concentrate and observe their own tremors. In a training phase the patient was asked, through biofeedback mechanism, to control their tremors. Results were analyzed based on the frequency and intensity of the tremor signals over time. Left side stimulation on frontal electrode positions F3, FC3 and C3 of the coil were effective for controlling the tremors a few minutes after the stimulation.

What is claimed is:
1. A system comprising:
a Transcranial Magnetic Stimulation (TMS) machine;
a Transcranial Stimulation Biofeedback (TSB) Detector device;
a software component comprising instructions stored on one or more non-transitory computer readable media that, when executed by a computing device, direct the computing device to:
receive waveforms from the TSB Detector device;
compute a determination factor based on the waveforms; and
when the determination factor is outside a predetermined range, send an abort signal such that the TMS machine ceases providing magnetic stimulation, and
when the determination factor is not outside the predetermined range, allow the TMS machine to continue providing magnetic stimulation,
the TSB Detector device comprising:
a three-axis accelerometer sensor configured to provide three-dimensional signals;
a three-channel analog amplifier configured to receive the three-dimensional signals; and
a capacitor and a resistor connected between the three-axis accelerometer and the three-channel analog amplifier and configured to generate a cut-off frequency, and
three-dimensional tremor signals detected by the TSB Detector device being synchronized with the TMS machine via a dual communication link.
2. The system of claim 1, wherein the determination factor is a component of a tremor waveform of the waveforms received from the TSB Detector device.
3. The system of claim 1, wherein the predetermined range of the determination factor is based on a patient baseline obtained by the TSB Detector device.
4. The system of claim 1, wherein the predetermined range is a patient baseline range obtained by the TSB Detector device, plus a variability factor extending each endpoint of the patient baseline range.
5. The system of claim 4, wherein the variability factor is a patient variability factor and is determined by a user.
6. The system of claim 4, wherein the variability factor is 10%.
7. The system of claim 1, wherein the software component further comprises instructions that direct the computing device to:
receive an indication of a user input; and
send a control instruction to perform an operation on the TMS machine based on the user input.
8. The system of claim 7, wherein the software component further comprises
instructions that direct the computing device to:

render a graphical user interface for indicating the user input.

9. The system of claim 7, wherein the operation comprises one or more of:
abort magnetic stimulation;
trigger a magnetic pulse with a predefined intensity;
increase intensity of the magnetic pulse; and
decrease intensity of the magnetic pulse.

10. The system of claim 1, further comprising a hardware component comprising an integrated circuit, wherein the integrated circuit is in operable communication with the TMS machine, wherein sending the abort signal such that the TMS machine ceases providing magnetic stimulation comprises sending the abort signal to the hardware component, wherein the hardware component directs the TMS machine to cease providing magnetic stimulation.

11. The system of claim 10,
wherein the TMS machine comprises a plurality of pedals, wherein each pedal directs a mode of operation of the TMS machine,
wherein the hardware component comprises at least one solenoid disposed adjacent to a pedal of the plurality of pedals of the TMS machine, and
wherein, in response to receiving a control instruction from the software component, the hardware component activates a solenoid of the at least one solenoid.

12. The system of claim 11, wherein the mode of operation of the TMS machine comprises one or more of:
abort magnetic stimulation;
trigger a magnetic pulse with a predefined intensity;
increase intensity of the magnetic pulse; and
decrease intensity of the magnetic pulse.

13. The system of claim 11, wherein the software component further comprises instructions that direct the computing device to:
receive an indication of a user input; and
send the control instruction to the hardware component based on the user input.

14. The system of claim 10, wherein the integrated circuit is in operable communication with the TSB Detector device, and wherein the software component receives the waveforms from the TSB Detector device via the hardware component.

15. A method for controlling magnetic stimulation to a patient, the method comprising:
determining a current tremor state of the patient's tremor based on at least one waveform of a TSB Detector device connected to the patient; and
controlling magnetic stimulation to the patient based on the current tremor state;
the TSB Detector device comprising:
a three-axis accelerometer sensor configured to provide three-dimensional signals;
a three-channel analog amplifier configured to receive the three-dimensional signals; and
a capacitor and a resistor connected between the three-axis accelerometer and the three-channel analog amplifier and configured to generate a cut-off frequency, and
three-dimensional tremor signals detected by the TSB Detector device being synchronized with a Transcranial Magnetic Stimulation TMS machine via a dual communication link.

16. The method of claim 15, wherein controlling magnetic stimulation to the patient comprises providing a control signal that controls the generation of or level of magnetic stimulation provided by the TMS machine.

17. The method of claim 16, wherein controlling magnetic stimulation to the patient comprises preventing any magnetic stimulation by the TMS machine when a determination factor of the patient's tremor falls outside a predetermined range.

18. The method of claim 17, wherein the predetermined range is based on a baseline range of the patient plus a variability factor extending each endpoint of the baseline range.

19. The method of claim 18, wherein the variability factor is based on the patient and is determined by a user input.

* * * * *